(12) United States Patent
Hirata

(10) Patent No.: US 6,432,674 B1
(45) Date of Patent: Aug. 13, 2002

(54) STEROID HORMONE BINDING PROTEIN

(75) Inventor: Yuichi Hirata, Niihari-mura (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/565,808

(22) Filed: May 5, 2000

Related U.S. Application Data

(63) Continuation-in-part of application No. PCT/JP98/05010, filed on Nov. 6, 1998.

Foreign Application Priority Data

Nov. 7, 1997 (JP) ............................................. 9-322376

(51) Int. Cl.⁷ ......................... C12P 21/06; C12N 15/00; C12N 5/06; C07H 21/02
(52) U.S. Cl. ...................... 435/69.1; 435/6; 435/320.1; 435/325; 536/23.5
(58) Field of Search .................... 530/350; 435/69.1, 435/6, 320.1, 325; 536/23.5

(56) References Cited

PUBLICATIONS

Sambrook et al., (1989). Molecular Cloning: A laboratory Manual. pp. 16.20–16.67.*

Gerdes,D. (1997). NCBI Sequence Viewer.*

Meyer et al., "Purification and partial . . . ," Eur. J. Biochem., 239:726–731, 1996.

Meyer et al., "Characterization and solubilization . . . ," Eur. J. Biochem., 229:736–740, 1995.

Falkenstein et al., "Full–Length cDNA . . . ," Biochemical and Biophysical Research Communications, 229:86–89, 1996.

* cited by examiner

*Primary Examiner*—Jeffrey Stucker
*Assistant Examiner*—Jegatheesan Seharaseyon
(74) *Attorney, Agent, or Firm*—Fish & Richardson P.C.

(57) ABSTRACT

Several ESTs deduced as a part of a cDNA encoding a protein that is homologous with a membrane-bound steroid binding protein PMBP were found. Based on the sequence data of these ESTs, a consensus sequence was extracted, and primers were designed based on this consensus sequence. Using the thus designed primers, a polymerase chain reaction of human genes was effected. As a result, a gene encoding a novel steroid hormone binding protein that is homologous with PMBP was successfully isolated from a human for the first time.

17 Claims, 3 Drawing Sheets

```
              1                                                            50
Pig PMBP                                             MAAGDVAL TGADPSELEG
Rat 25dx                                             MAAGDVVL TGADPSELEG
  hSMBP1                                             MAAGDVVL TGADPSDLES
  hSMBP2  MAAGDGDVKL GTLGSGSESS NDGGSESPGD AGAAAGGGW AAAALALLTG 51                                                            100
Pig PMBP  GGLLHEIPTS PLNLLDLGLG IFLLYKIVEG DQPAAS.DSD DDEPPPLPRL
Rat 25dx  GGLLQEIETS PLNLLLGLG IFLLYKIVRG DQPGASQDND DDEPPPLPRL
  hSMBP1  GGLLHEIPTS PLNLLLGLG IFLLYKIVRG DQPAASQDSD DDEPPPLPRL
  hSMBP2  GGEML.LNVA LVADVLLG.A YRLWVRNGRR GLGAGAGAGE ESPATSLPRM 101                                                            150
Pig PMBP  RRDFTPAEL RRFDGVQDPR ILMAINGKVF DVTKGRKFYG PEGPYGVFAG
Rat 25dx  RRDFTPAEL RRYDGVQDPR ILMAINGKVF DVTKGRKFYG PEGPYGVFAG
  hSMBP1  RRDFTPAEL RRFDGVQDPR ILMAINGKVF DVTKGRKFYG PEGAYGVPAG
  hSMBP2  KRDFSLEQL RQYDGSRNPR ILLAVNGKVF DVTKGSKFYG PAGPYGIFAG 151                                                            200
Pig PMBP  RDASRGEATF CLDKEALKDE YDDESDLTPA QQETLNDWDS QFTFKYHHV.
Rat 25dx  RDASRGLATF CLDKEALKDE YDDESDLTPA QQETLNDWDS QFSSPSTIT
  hSMBP1  RDASRGEATF CLDKEALKDE YDDLSDLTAL QQETLSDWES QFTFKYHHV.
  hSMBP2  RDASRGLATF CLDKDALRDE YDDLSDLNAV QMESVRENEM QFKEKYDYV.

201                                                            250
Pig PMBP  .GKLLEGEE PTWSDEEBP KDESARKND
Rat 25dx  WGKLLEGALE PIVYSDDELQ KMRLLGRVTE AVSGAYLFLY PAKSFVTFQS
  hSMBP1  .GKLLEGEE PTWSDEEBP KDESARKND
  hSMBP2  .GLLLKGEE LSEYTDEEDT KDHNKQD

251
Pig PMBP
Rat 25dx  VFTTW
  hSMBP1
  hSMBP2
```

FIG. 1 hSMBP1
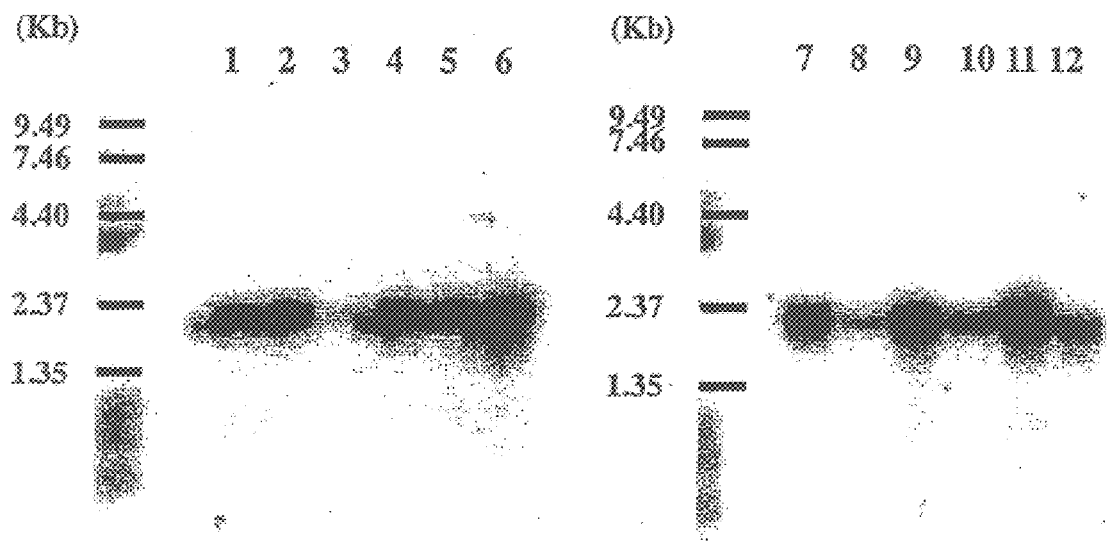
hSMBP2
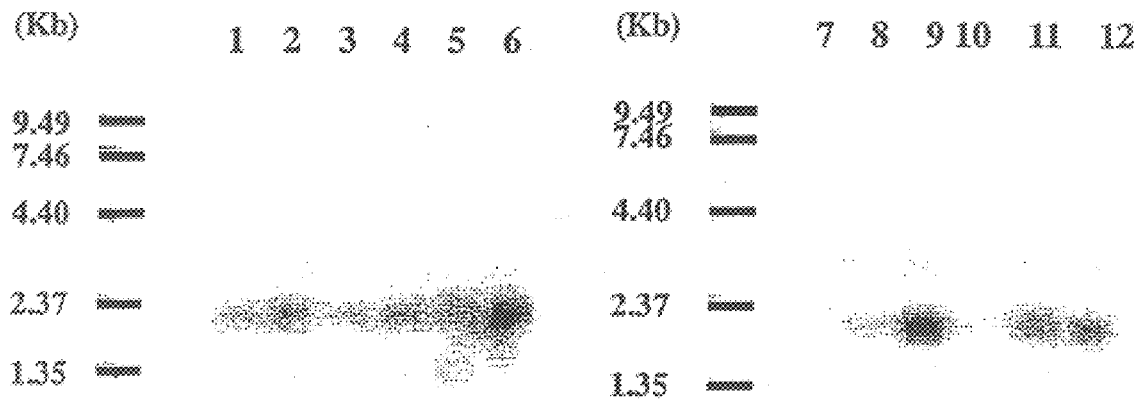
FIG. 3

STEROID HORMONE BINDING PROTEIN

This is a continuation-in-part of PCT/JP98/05010, filed Nov. 6, 1998, and claims priority from Japanese Patent Application No. 9/322376, filed Nov. 7, 1997.

TECHNICAL FIELD

The present invention relates to steroid hormone binding proteins, genes thereof, and production and use of the proteins and the genes.

BACKGROUND ART

It is generally thought that steroid hormones exert their physiological influence by regulating transcriptional activities. Very recently, however, steroids that exhibit their activities rapidly without acting on genes have become widely known, but this cannot be explained by the above theory. Evidence of this rapid action of steroids has been shown for every steroid in many species and tissues. Examples include the rapid action of aldosterone on lymphocytes and vascular smooth muscle (Wehling, M. (1995) Cardiovasc. Res. 29(2), 167–171), vitamin D3 on epithelial cells, progesterone on sperm (Revelli, A.; Modotti, M.; Piffaretti-Yanez, A.; Massobrio, M.; and Balerna, M. (1994) Hum Reprod 9 (5), 760–766), neurosteroids on neurons, and estrogen on blood vessels. The signal recognition and transduction mechanisms of these activities are currently being studied. As a result, it is now becoming clear that the signal recognition and transduction system resembles cascade systems of membrane receptors and the second messengers, such as those of catecholamines and peptide hormones, since many of the activities depend on phospholipase C, phosphoinositide turnover, intracellular pH, intracellular calcium, protein kinase C, tyrosine kinases, etc., (Baran, D. T. (1994) J Cell Biochem 56 (3), 303–306; de Boland, A. R. and Nemere, I. (1992) J Cell Biochem 49 (1), 32–36). Although the physiological or pathological relevance is not clear, it has been presumed that the rapid action of steroids can also be observed in vivo in the cardiovascular system, the central nervous system, and the reproductive system. It was expected that these receptors would be cloned soon and that the relationship between the rapid action of steroids and their clinical effects would be clarified (Wehling, M. (1997) Annu Rev Physiol 59, 365–393; and Wehling, M. (1995) J Mol Med 73 (9), 439–447).

In recent years, the progesterone membrane binding protein (PMBP), a membrane binding type that differs from usual steroid hormone receptors of the intranuclear transcription regulation type, was finally cloned for the first time from a pig (Falkenstein, E.; Meyer, C.; Eisen, C.; Scriba, P. C.; and Wehling, M. (1996) Biochem Biophys Res Commun 229 (1), 86–89). This protein was purified from the microsome fraction, has a hydrophobic region near its N terminus, and shows no homology to existing steroid receptors. To date, a putative human homologue of PMBP, the "putative progesterone binding protein gene" (LOCUS, HSPROGBIN; accession number, Acc.Y12711), and a putative rat homologue, "25Dx" (LOCUS, RNU63315; accession number, Acc.U63315), have been isolated. The pig PMBP has been well characterized, and it has been reported to bind not only to progesterone but also to corticosterone, cortisol, promegestone, and testosterone (Meyer C. (1996) Eur. J. Biochem. 239, 726–731).

The discovery of these membrane-bound steroid hormone binding proteins suggests the existence of a mechanism in the organism for regulating hormone action that differs from the one for the receptors involved in the intranuclear transcription regulation. Therefore, it should be possible to develop novel drugs that distinguish the affinities or biological activities of the membrane-bound steroid hormone binding proteins from those of the intranuclear transcription regulation type receptors using the membrane-bound steroid hormone binding proteins.

DISCLOSURE OF THE INVENTION

An objective of the present invention is to provide a novel steroid hormone binding protein having homology to PMBP and its gene, and also methods for producing it and uses thereof.

In order to achieve the above objective, the present inventors discovered ESTs that are inferred to be parts of a cDNA encoding a protein having homology to PMBP (Falkenstein, E.; Meyer, C.; Eisen, C.; Scriba, P. C.; and Wehling, M. (1996) Biochem Biophys Res Commun 229 (1), 86–89), which is a membrane-bound steroid hormone binding protein. The present inventors then extracted a consensus sequence from the sequence information of the ESTs and performed a polymerase chain reaction on human genes using primers designed according to the consensus sequence. As a result, they have succeeded for the first time in isolating the gene encoding a novel steroid hormone binding protein having homology to PMBP from a human.

The present invention relates to a novel steroid hormone binding protein having homology to PMBP and its gene, and also methods for producing it and uses thereof. More specifically, it relates to:

(1) a protein comprising the amino acid sequence of SEQ ID NO:4, (2) a protein having a steroid hormone-binding activity, comprising the amino acid sequence of SEQ ID NO:4 wherein one or more amino acids are substituted, deleted, and/or added, (3) a DNA encoding the protein of (1) or (2), (4) a vector carrying the DNA of (3), (5) a transformant expressibly retaining the DNA of (4), (6) a method for producing the protein of (1) or (2), the method comprising culturing the transformant of (5), (7) an antibody that binds to the protein of (1), (8) a method for screening a compound that binds to the protein of (1) or (2), the method comprising selecting a compound that binds to the protein of (1) or (2) by contacting a test sample with the protein of (1) or (2), (9) a compound that binds to the protein of (1),

(10) the compound of (9) isolable by the method of (8),

(11) a method for screening a compound that specifically binds to the protein of (1) or (2) or a steroid hormone receptor of the intranuclear transcription regulation type, the method comprising selecting a compound that specifically binds to the protein of (1) or (2) or the steroid hormone receptor of the intranuclear transcription regulation type by contacting a test sample with the protein of (1) or (2) and the steroid hormone receptor of the intranuclear transcription regulation type,

(12) a compound that specifically binds to either the protein of (1) or (2) or the steroid hormone receptor of the intranuclear transcription regulation type,

(13) the compound of (12) isolable by the method of (11), and

(14) a DNA comprising at least 15 nucleotides, which specifically hybridizes with a DNA comprising the nucleotide sequence of SEQ ID NO:3.

The present invention also relates to a protein of human origin, "hSMBP2," which has homology to the pig membrane-bound progesterone binding protein (progesterone membrane binding protein (PMBP)) (Falkenstein, E.; Meyer, C.; Eisen, C.; Scriba, P. C.; and Wehling, M. (1996) Biochem Biophys Res Commun 229 (1), 86–89). The nucleotide sequence of the hSMBP2 cDNA isolated by the present inventors is shown in SEQ ID NO:3, and the amino acid sequence of the protein encoded by the cDNA is shown in SEQ ID NO:4.

FIG. 1 compares the amino acid sequence of hSMBP2 and those of proteins having homology to it, pig PMBP, rat 25Dx, and hSMBP1. hSMBP1, like hSMBP2, is a human gene isolated by polymerase chain reaction (PCR) using primers designed according to consensus sequences extracted from multiple ESTs having homology to pig PMBP. A gene identical to hSMBP1 has been registered in a database (Acc. Y12711). As apparent from FIG. 1, although hSMBP2 has significant homology to pig PMBP, it has a somewhat lower degree of homology except near its C terminus, unlike hSMBP1, which has a high degree of homology as a whole. hSMBP2 is thus presumed to be a protein belonging to the same family but having a different spectrum of steroids to bind.

The steroid hormone binding protein of the present invention is thought to be a membrane-bound type, which differs from the usual intranuclear transcription regulation receptors. This suggests that it may be involved in regulating hormone action in the organism by a different mechanism than the intranuclear transcription regulation receptors. It therefore may be possible to develop drugs that have few side effects using the steroid hormone binding protein of the present invention as the target by taking advantage of the difference in binding affinities between it and the intranuclear transcription regulation type receptors with regard to steroid hormones. In particular, since hSMBP2 is derived from a human, it has clinical development advantages over proteins derived from other mammalian species such as pigs.

The steroid hormone binding protein of the present invention can be prepared either as a recombinant protein using the genetic recombination technology or as a natural protein. For example, it can be prepared as a recombinant protein by incorporating the DNA encoding the steroid hormone binding protein of the present invention (for example a DNA having the nucleotide sequence of SEQ ID NO:3) into an appropriate expression vector, introducing it into a host cell, and purifying the protein from the transformant thus obtained. It can also be prepared as a natural protein by first preparing a column using the antibody obtained from a small animal immunized with the prepared recombinant protein, then performing affinity chromatography on the extracts from the tissues or cells that highly express the steroid hormone binding protein of the present invention (for example testis or cancer cells) using the said column.

The present invention also includes proteins that are functionally equivalent to hSMBP2 protein. Here "functionally equivalent" means that the protein in question has binding activity for steroid hormones similar to the hSMBP2 protein. "Having steroid hormone-binding activity" means that the protein has an activity to bind to at least one kind of steroid hormone. Steroid hormone-binding activity can be detected, for example, by testing for binding activity using commercially available tritium-labeled steroid hormones.

Proteins that are functionally equivalent to the hSMBP2 protein can be prepared by mutating the amino acid sequence of the hSMBP2 protein. As an example, one can introduce an appropriate substitution or other modification that does not affect its function into the steroid hormone binding protein of the present invention having the amino acid sequence described in SEQ ID NO.:4, resulting in the isolation of a protein that is functionally equivalent to the hSMBP2 protein. The steroid hormone binding protein of the present invention also includes proteins that are functionally equivalent to the hSMBP2 protein and that have amino acid sequences resulting from the substitution, deletion, and/or addition of one or more amino acid to the amino acid sequence described in SEQ ID NO:4.

The term "substantially pure" as used herein in reference to a given polypeptide means that the polypeptide is substantially free from other biological macromolecules. The substantially pure polyp pried is at least 75% (e.g., at least 80, 85, 95, or 99%) pure by dry weight. Purity can be measured by any appropriate standard method, for example, by column chromatography polyacrylamide gel electrophoresis, or HPLC analysis.

Methods of mutating amino acid sequences of proteins include a site-specific mutagenesis system using PCR (GIBCO-BRL, Gaithersburg, Md.) and a site-specific mutagenesis method using oligonucleotides (Kramer, W. and Fritz, H. J. (1987) Methods in Enzymol., 154: 350–367). There are no restrictions on the number of amino acids to be mutated as long as the steroid hormone-binding activity is retained. However, the number of amino acids to be mutated is usually 30 amino acids or less, preferably 20 amino acids or less, more preferably 10 amino acids or less, and still more preferably 5 amino acids or less.

A "conservative amino acid substitution" is one in which an amino acid residue is replaced with another residue having a chemically similar side chain. Families of amino acid residues having similar side chains have been defined in the art. These families include amino acids with basic s de chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

It is also possible that amino acid mutations within a protein occur naturally, and the steroid hormone bindin protein of the present invention also includes such mutant proteins as produced in this manner.

Other methods o preparing proteins that are functionally equivalent to the hSMBP2 protein include using the hybridization technique. Specifically, a person skilled in the art can use a well-known hybridization technique (Sambrook, J. et al., Molecular Cloning 2nd ed. 9.47–9.58, Cold Spring Harbor Lab. Press, 1989) to isolate a DNA having a high degree of homology to the DNA sequence encoding the "hSMBP2" protein by using the DNA sequence (SEQ ID NO:3) or a part thereof, and obtain a protein that is functionally equivalent to the "hSMBP2," protein by means of the said DNA. The steroid hormone binding protein of the present invention also includes proteins encoded by DNAs capable of hybridizing with DNAs comprising the DNA sequence described in SEQ ID NO:3 and that are functionally equivalent to the hSMBP2 protein.

Hybridization stringencies, as used herein, are defined as about 52° C., 2×SSC, 0.01% SDS (low stringency); about 50° C., 2×SSC, 0.01% SDS (medium stringency); or about 65° C., 2×SSC, 0.01% SDS (high stringency). As the above indicates, higher temperatures are expected to yield more isolation of DNA having high homology. A person skilled in the art can realize similar stringency by considering, in addition to the temperature, such factors as the probe concentration, probe length, salt strength, and reaction time, as the hybridization stringency.

The protein encoded by the DNA obtained by means of the hybridization technique usually has a high degree of homology to the hSMBP2 protein (SEQ ID NO:4) in terms of the amino acid sequence. "A high degree of homology" means 40% or more homology, preferably 60% or more homology, and more preferably 80% or more homology. The "percent identity" of two amino acid sequences or of two nucleic acids is determined using the algorithm of Karlin and Altschul (Proc. Natl. Acad. Sci. USA 87:2264–2268, 1990), modified as in Karlin and Altschul (Proc. Natl. Acad. Sci. USA 90:5873–5877, 1993). Such an algorithm is incorporated into the NBLAST and XBLAST programs of Altschul et al. (J. Mol. Biol. 215:403–410, 1990). BLAST nucleotide searches are performed with the NBLAST program, scor=100, wordlength=12. BLAST protein searches are performed with the XBLAST program, score= 50, wordlength=3. Where gaps exist between two sequences, Gapped BLAST is utilized as described in Altschul et al. (Nucleic Acids Res. 25:3389–3402, 1997). When utilizing BLAST and Gapped BLAST programs, the default parameters of the respective programs (e.g., XBLAST and NBLAST) are used. See http://www.ncbi.nlm.nih. gov.

The present invention also relates to DNAs encoding the steroid hormone binding protein of the present invention. There are no particular restrictions concerning the DNA of the present invention as long as it can encode the steroid hormone binding protein of the present invention, and it includes cDNAs, genomic DNAs, and chemically synthesized DNAs. cDNAs can be prepared, for example, by preparing primers based on the nucleotide sequence described in SEQ ID NO:3 and performing RT-PCR. Genomic DNAs can be prepared by the plaque hybridization method using λphage. The nucleotide sequences of the DNAs thus obtained can be determined by an ordinary method using, for example, a commercially available dye terminator sequencing kit (Applied Biosystems).

An "isolated nucleic acid" is a nucleic acid the structure of which is not identical to that of any naturally occurring nucleic acid or to that of any fragment of a naturally occurring genomic nucleic acid spanning more than three separate genes. The term therefore covers, for example, (a) a DNA which has the sequence of part of a naturally occurring genomic DNA molecule but is not flanked by both of the coding sequences that flank that part of the molecule in the genome of the organism in which it naturally occurs; (b) a nucleic acid incorporated into a vector or into the genomic DNA of a prokaryote or eukaryote in a manner such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein. Specifically excluded from this definition are nucleic acids present in mixtures of different (i) DNA molecules, (ii) transfected cells, or (iii) cell clones: e.g., as these occur in a DNA library such as a cDNA or genomic DNA library.

The present invention also relates to vectors into which the DNA of the present invention is inserted. There are no particular restrictions concerning the vectors into which the DNA of the present invention is inserted, and a variety of vectors can be used according to the purposes. The vectors to express the steroid hormone binding protein of the present invention in vivo (for gene therapy as an example) and the vectors to prepare the recombinant protein are included. The vectors to express the steroid hormone binding protein of the present invention in vivo include the adenovirus vector "pAdexLcw" and the retrovirus vector "pZlPneo." Expression vectors are especially useful when one wishes to use vectors to produce the steroid hormone binding protein of the present invention. Vectors such as pQE vector (Qiagen, Hilden, Germany) are preferable as the expression vectors if one wishes to use *E. coli*, "SP-Q01" (Stratagene, La Jolla, Calif.) if one wishes to use yeast, and BAC-to-BAC baculovirus expression system (GIBCO-BRL, Gaithersburg, Md.) if one wishes to use insect cells. If mammalian cells such as CHO, COS, or NIH-3T3 cells are used, vectors such as the LacSwitch II expression system (Stratagene, La Jolla, Calif.) are suitable. The DNA of the present invention can be inserted into a vector using a standard method (for example, refer to "The Qiaexpressionist handbook, Qiagen, Hilden, Germany").

The present invention also relates to transformants retaining the DNA of the present invention in an expressible state. The transformants of the present invention include those that retain the vectors into which the DNA of the present invention is inserted and those that have the DNA of the present invention integrated into the host genome. However, they can also include all other forms as long as they expressibly retain the DNA of the present invention. There are no particular restrictions concerning the cells into which the vectors of the present invention are to be introduced. If one wishes to express the steroid hormone binding protein of the present invention in vivo, one can use desired cells as the target cells. For example, one can use *E. coli*, yeast, animal cells, or insect cells to produce the steroid hormone binding protein of the present invention. Vectors can be introduced into the cells, for example, by the electroporation and the calcium phosphate methods. A recombinant protein can be isolated and purified from a transformant constructed to produce the recombinant protein by a standard method such as those described in the literature "The Qiaexpressionist handbook, Qiagen, Hilden, Germany."

The present invention also relates to antibodies that bind to the steroid hormone binding protein of the present invention. There are no particular restrictions concerning the form of the antibody of the present invention, and it may include monoclonal antibodies as well as polyclonal antibodies. The antibodies also include the antisera obtained by immunizing rabbits or other small animals with the steroid hormone binding protein of the present invention, polyclonal antibodies and monoclonal antibodies of all classes, humanized antibodies by gene recombination, and human antibodies. They also include single-stranded antibodies, and parts of antibodies such as Fab fragments and $F(ab')_2$ fragments.

The antibodies of the present invention can be prepared by the method in the following example. To prepare a polyclonal antibody, one could obtain sera by immunizing small animals such as rabbits with the steroid hormone binding protein of the present invention, applying the sera onto an affinity column coupled with the steroid hormone binding protein of the present invention, and obtaining the fraction that recognizes only the steroid hormone binding protein of the present invention. Next, one could prepare immunoglobulin G or M from this fraction by purification through a protein A or protein G column. To prepare a monoclonal antibody, one could immunize small animals such as mice with the steroid hormone binding protein of the present invention, remove the spleen from the mice, grind it into individual cells, fuse them with mouse myeloma cells utilizing reagents such as polyethylene glycol, and select the clones that produce the antibodies against the steroid hormone binding protein of the present invention from the fusion cells (hybridomas) thus created. Next, one could transplant the hybridomas obtained into the abdominal cavity of a mouse and recover the ascites from the mouse. By purifying the monoclonal antibody thus obtained by ammonium sulfate precipitation, a protein A or a protein G column, DEAE ion exchange chromatography, or an affinity column coupled with the steroid hormone binding protein of the present invention, one could obtain the preparation.

In addition to purifying or detecting the steroid hormone binding protein of the present invention, the antibodies of the present invention can also be used as drugs to promote or inhibit the signal transduction of the steroid hormone binding protein of the present invention. When administering the antibodies to humans as drugs, human antibodies or humanized antibodies are effective in terms of immunogenicity. Human antibodies can be prepared, for example, by immunizing a mouse whose immune system is replaced by a human system with the steroid hormone binding protein of the present invention. Humanized antibodies, on the other hand, can be prepared, for example, by the CDR graft method in which the antibody gene is cloned from the monoclonal antibody producing cells, and its antigenic determinant is grafted onto an existing human antibody.

The present invention also relates to methods for screening the compounds that bind to the steroid hormone binding protein of the present invention. The screening method of the present invention includes a process of selecting compounds that bind to the steroid hormone binding protein of the present invention by bringing a test sample into contact with the steroid hormone binding protein of the present invention. There are no particular restrictions concerning the test sample brought into contact with the steroid hormone binding protein of the present invention, and test samples include cell extracts, synthetic low molecular weight compound libraries, expression products of gene libraries, and synthetic peptide libraries.

A person skilled in the art can use the method below to isolate proteins that bind to the steroid hormone binding protein of the present invention or the genes thereof, using the protein of the present invention. Specifically, proteins that bind to the steroid hormone binding protein of the present invention or the genes thereof can be prepared by, for example, first constructing a cDNA library from the cells expected to express proteins that bind to the steroid hormone binding protein of the present invention (such as testis tissues or ovary tissues) using a phage vector (such as λgt11 or ZAP), expressing it on LB-agarose, fixing the expressed proteins onto a filter, purifying the steroid hormone binding protein of the present invention as a biotin-labeled protein or a fusion protein with the GST protein, letting it react with the filter above, and detecting the plaques expressing the proteins that bind to the steroid hormone binding protein of the present invention using streptavidin or an anti-GST antibody. This method is called the "West-western blotting method" (Skolnik, E. Y.; Margolis, B.; Mohammadi, M.; Lowenstein, E.; Fisher, R.; Drepps, A.; Ullrich, A.; and Schlessinger, J. (1991) Cloning of PI13 kinase-associated p85 utilizing a novel method for expression/cloning of target proteins for receptor tyrosine kinases. Cell 65, 83–90).

It is also possible to prepare proteins or the genes thereof that bind to the steroid hormone binding protein of the present invention using the two hybrid system (MATCHMAKER Two-Hybrid System, Mammalian MATCHMAKER Two-Hybrid Assay Kit, MATCHMAKER One-Hybrid System (all from Clontech), HybriZAP Two-Hybrid Vector System (Stratagene) and the paper by Dalton, S. and Treisman, R. (1992) titled "Characterization of SAP-1, a protein recruited by serum response factor to the c-fos serum response element," Cell 68, 597–612). In this method, the steroid hormone binding protein of the present invention is expressed in yeast cells as a fusion protein with the SRF binding domain or the GAL4 binding domain. A cDNA library is next prepared from the cells expected to express proteins that bind to the steroid hormone binding protein of the present invention so that the protein is expressed as a fusion protein with the VP16 or the GAL4 transcription activation domain. The cDNA library is then introduced into the above yeast cells, and the library-derived cDNA is isolated from the positive clones. (When a protein that binds to the steroid hormone binding protein of the present invention is expressed in the yeast cell, the binding between the two proteins will activate a reporter gene, which makes it possible to confirm the positive clone.)

Furthermore, it is also possible to prepare proteins or the genes thereof that bind to the steroid hormone binding protein of the present invention. This may be done by applying the culture supernatants or the extracts of the cells expected to express proteins that bind to the steroid hormone binding protein of the present invention onto an affinity column coupled with the steroid hormone binding protein of the present invention then purifying the proteins that specifically bind to the column. It is further possible to obtain the DNA encoding the said proteins by analyzing the amino acid sequence of the protein thus obtained, synthesizing an oligo-DNA based on that information, and screening a cDNA library with the said DNA as a probe.

The method of screening for binding molecules by applying synthetic compounds, a natural product bank, or a random phage peptide display library to the fixed steroid hormone binding protein of the present invention, and the method of isolating low molecular weight compounds, proteins (or the genes thereof), or peptides that bind to the steroid hormone binding protein of the present invention, by high throughput screening using a combinatorial chemistry technique (Wrighton, N. C.; Farrell, F. X.; Chang, R.; Kashyap, A. K.; Barbone, F. P.; Mulcahy, L. S.; Johnson, D. L.; Barrett, R. W.; Jolliffe, L. K.; and Dower, W. J., Small peptides as potent mimetics of the protein hormone erythropoietin. Science (UNITED STATES) Jul. 26, 1996, 273 pp458–64; Verdine G L., The combinatorial chemistry of nature. Nature (ENGLAND) Nov. 7, 1996, 384 pp11–13; and Hogan, J. C. Jr. Directed combinatorial chemistry. Nature (ENGLAND) Nov. 7, 1996, 384 pp17–9) are also well known to a person skilled in the art. The compounds isolated through the methods above could be applied as drugs to promote or inhibit the activities of the steroid hormone binding protein of the present invention.

By performing similar screening procedures using a steroid hormone receptor of the intranuclear transcription regulation type and the steroid hormone binding protein of the present invention, it is also possible to screen for compounds that bind specifically to either of the two. In particular, one can bring test samples into contact with the steroid hormone binding protein of the present invention and with the steroid hormone receptor of the intranuclear transcription regulation type then select the compounds that bind specifically to either the steroid hormone binding protein of the present invention or the steroid hormone receptor of the intranuclear transcription regulation type. In this way, one can screen for compounds that bind specifically to either the steroid hormone binding protein of the present invention or the steroid hormone receptor of the intranuclear transcription regulation type. The known steroid hormone receptors of the intranuclear transcription regulation type used for this screening include progesterone receptor (Acc. 189935), glucocorticoid receptor (Acc. 121069), androgen receptor (Acc. 105325), vitamin D receptor (Acc. 340203), mineral corticoid receptor (Acc. 126885), estrogen receptor (Acc. 544257), steroid hormone receptor ERR1(Acc. 119560), and steroid hormone receptor ERR2 (Acc. 119561). These compounds can be used to suppress the side effects of the known steroid type drugs.

A compound isolated by the screening method of the present invention for use as a medicine can be formulated by means of known pharmaceutical formulation manufacturing methods. For example, the compound is administered to the patient using pharmaceutically acceptable carriers or media (isotonic sodium chloride solutions, vegetable oils, suspending agents, surfactants, stabilizers, etc.). Administration can be made percutaneously, intranasally, perbronchially, intramuscularly, intravenously, or perorally, depending on the characteristics of the compound. If the isolated compound is a DNA, it can be administered to the humans by utilizing the vectors for in vivo expression described above.

The present invention also relates to DNAs having a chain length of at least 15 nucleotides that hybridize specifically with DNAs comprising the nucleotide sequence described in SEQ ID NO:3 (including its complementary strand). Here, "hybridize specifically" means that there is no significant cross-hybridization with DNAs encoding other proteins under standard hybridization conditions, and preferably under stringent hybridization conditions. Such DNAs can be used as probes to detect or isolate the DNA encoding the proteins of the present invention and as primers to amplify the same. A person skilled in the art can select the appropriate stringency needed for the specific hybridization by considering such parameters as hybridization temperature, reaction time, probe or primer concentration, probe or primer length, and salt strength.

Furthermore, the "DNAs comprising at least 15 nucleotides that hybridize specifically with DNAs comprising the nucleotide sequence described in SEQ ID NO:3" of the present invention include, for example, antisense oligonucleotides and ribozymes. Antisense oligonucleotides act on the cells that produce the protein of the present invention, bind to the DNA or mRNA encoding the said protein, and suppress the protein's action through suppressing the expression of the protein of the present invention by inhibiting the transcription or translation, or by promoting the mRNA degradation. The antisense oligonucleotides include those that hybridize with the nucleotide sequence described in SEQ ID NO:3 at some positions. The antisense oligonucleotides are preferably antisense oligonucleotides against 15 or more consecutive nucleotides within the nucleotide sequence described in SEQ ID NO:3. More preferably, the antisense oligonucleotides are the above antisense oligonucleotides in which the above 15 or more consecutive nucleotides include a translation initiation codon.

The antisense oligonucleotides can be derivatives or modifications. These modifications include, for example, lower alkylphosphonate modifications such as the methylphosphonate type or the ethylphosphonate type, phosphorothioate modifications, and phosphoramidate modifications.

The antisense oligonucleotides include not only those that are completely complementary to the corresponding nucleotides constituting the given region of the DNA or mRNA, but also those that may contain one or more mismatches, as long as the oligonucleotides can selectively and stably hybridize with the DNA or mRNA of the nucleotide sequence described in SEQ ID NO:3. Such a DNA has at least 70%, preferably at least 80%, more preferably at least 90%, and still more preferably at least 95% nucleotide sequence homology in the region of at least a 15 consecutive nucleotide sequence. It is worth noting that the algorithm described in the literature cited above can be used to determine the homology.

The antisense oligonucleotides of the present invention can be made into external preparations such as paints and poultices by mixing with an appropriate base that is inactive toward the oligonucleotides. They can also be made into tablets, powders, granules, capsules, liposome capsules, injections, liquid preparations, or nasal drops by adding, if necessary, excipients, isotonizing agents, solubility increasing agents, stabilizers, antiseptics, and analgesic agents, or further made into freeze-dried preparations. These can be prepared according to standard methods.

BRIEF DESCRIPTION OF DRAWINGS

FIG. 1 compares amino acid sequences, aligning the hSMBP1 protein (SEQ ID NO:2), the hSMBP2 protein (SEQ ID NO:4), the pig PMBP protein (SEQ ID NO:4), and the rat 25dx protein(SEQ ID NO:22).

FIG. 3 shows electrophoretic images from northern blot analyses of hSMBP1 and hSMBP2. Lane 1 corresponds to lung, lane 2 to small intestine, lane 3 to muscle, lane 4 to prostate, lane 5 to testis, lane 6 to ovary, lane 7 to brain, lane 8 to heart, lane 9 to kidney, lane 10 to spleen, lane 11 to liver, and lane 12 to lymphocyte.

BEST MODE FOR CARRYING OUT THE INVENTION

Figure 2:
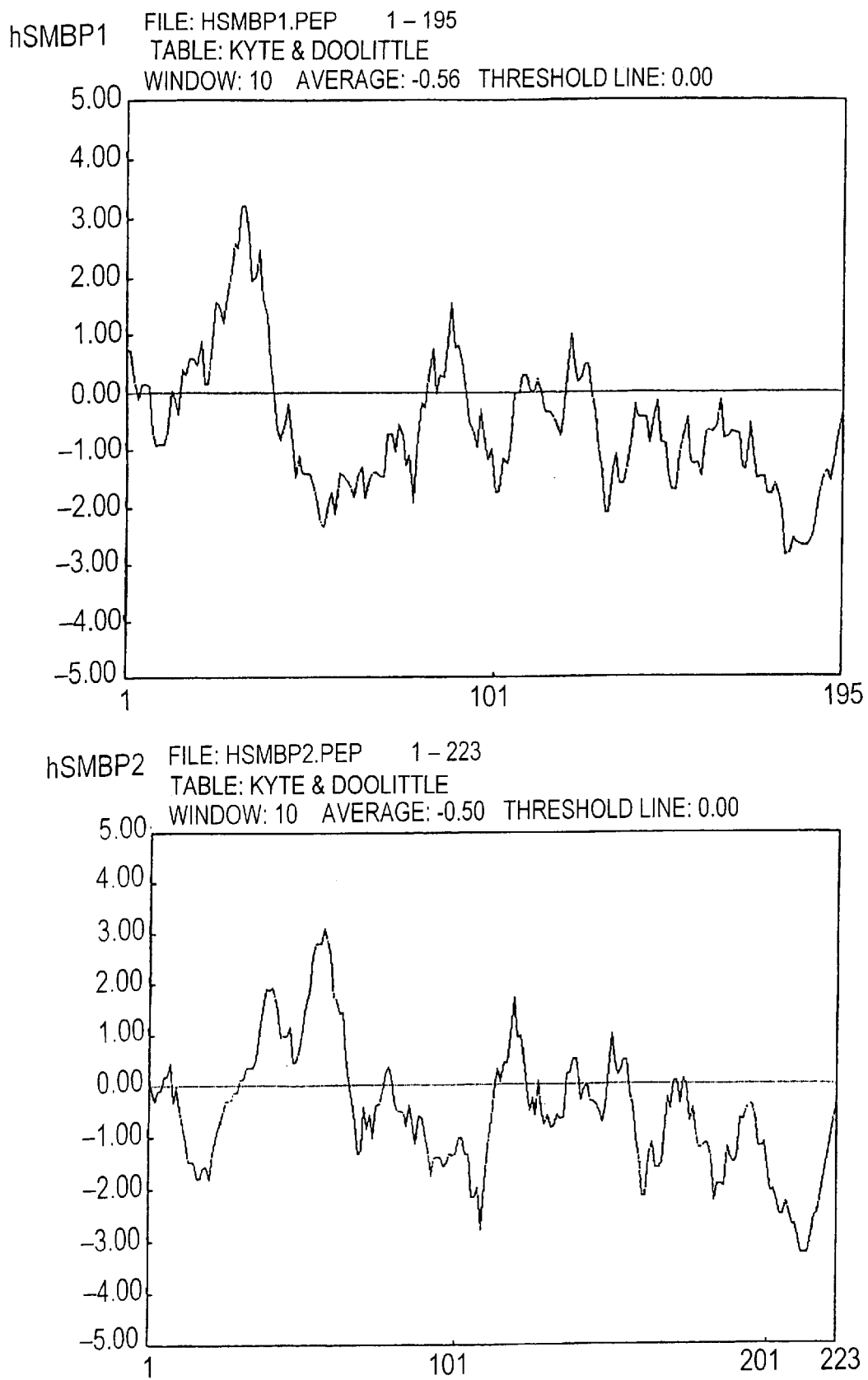
FIG. 2 illustrates hydrophobicity plots for the hSMBP1 protein and the hSMBP2 protein.

Embodiments of the present invention are exemplified below. However, the contents of the present invention shall in no way be limited by these examples.

EXAMPLE 1

Isolation of Membrane-bound Steroid Hormone Binding Proteins (hSMBP1 and hSMBP2)

The present inventors collected the EST sequences presumed to be parts of the cDNAs encoding the proteins that have homology to pig progesterone membrane binding protein (PMBP) from the Uni-gene of NCBI, arranged them based on homology, and extracted the consensus sequences. As a result, it became clear that the sequences can be divided into two groups, and because both groups were considered to be novel steroid binding proteins, the present inventors designated them "hSMBP1" and "hSMBP2" (human steroid membrane binding protein), and performed the following analysis. Twenty ESTs (AA021062, W56474, AA101294, AA116041, AA166645, W25549, H74052, AA081900, H23045, R59281, AA232394, AA080939, N52291, AA115422, H73490, N58287, H48290, H60595, R13334, and AA179573) were arranged for hSMBP1, and 17 ESTs (R31472, H02501, N27670, T49867, H55843, T85747, W47315, H72718, N36635, H72719, W47200, T90839, H55752, N20825, T49868, N26004, and R30936) were arranged for hSMBP2 to extract the consensus sequences.

From the consensus sequences above, the present inventors designed and synthesized the following primers. For hSMBP1, the present inventors designed primers hSMBP1-1 (SEQ ID NO:5: 5'-AAGAATTCCTGCCTA GCGCGGCCCAACCTTTACT-3') and hSMBP1-2 (SEQ ID NO:6:5'-GGGGATCCAAAAATAGATATACTT CCACTGAATG-3'); for hSMBP2, the present inventors designed primer hSMBP2-1 (SEQ ID NO:7: 5'-ACG GATCCTGAAGGCCCCTGACTTTGGTTGTTTA-3'). The present inventors performed an amplification reaction with hsMBP1 using Marathon-Ready cDNA, Kidney (Clontech) as the template, and hSMBP1-1 and hSMBP1-2 as the primers, according to the method recommended by the manufacturer. (Touchdown PCR: 94° C. for 1 minute; 5 cycles of 94° C. for 30 seconds and 72° C. for 4 minutes; 5 cycles of 94° C. for 30 seconds and for 4 minutes; and 25 cycles of 94° C. for 20 seconds and 68° C. for 4 minutes. Note that, instead of Advantage KlenTaq Polymerase Mix, TaKaRa Ex Taq (Takara Shuzo) and its accompanying buffer were used.) The DNA thus obtained was treated with restriction enzymes EcoRI and BamHI and cloned into the EcoRI-BamHI site of plasmid pCOS1. (The resulting plasmid was designated pCOS-hSMBP1.) The following primers (Table 1) internal to hSMBP1 were synthesized and used to determine the nucleotide sequence.

TABLE 1

| Primer | Sequence |
| --- | --- |
| hSMBP1-3 (SEQ ID NO:8) | 5'-GACCCAAGCGATCTGGAGAGC-3' |
| hSMBP1-4 (SEQ ID NO:9) | 5'-GGTGAAGTCGCGCCGCTTGAG-3' |
| hSMBP1-5 (SEQ ID NO:10) | 5'-CTCAAGCGGCGCGACTTCACC-3' |
| hSMBP1-6 (SEQ ID NO:11) | 5'-GGAAGCACTGAAGGATGA-3' |
| hSMBP1-7 (SEQ ID NO:12) | 5'-CATCCTTCAGTGCTTCCT-3' |

The present inventors performed an amplification reaction with hSMBP2 using Marathon-Ready cDNA, Placenta (Clontech) as the template and hSMBP2-1 and the AP-1 primer that came with the Marathon-Ready cDNA (SEQ ID NO: 13:5'-CCATCCTAATACGACTCACTATAGGGC-3') as the primers, according to the method recommended by the manufacturer. (Touchdown PCR: 94° C. for 1 minute; 5 cycles of 94° C. for 30 second seconds and 70° C. for 4 minutes; and 25 cycles of 94° C. for 20 seconds and 68° C. for 4 minutes. Note that TaKaRa Ex Taq (Takara Shuzo) and its accompanying buffer were used instead of Advantage KlenTaq Polymerase Mix.) The DNA thus obtained was treated with restriction enzymes EcoRI and BamHI, and cloned into the EcoRI-BamHI site of plasmid pCHO1. (The resulting plasmid was designated pCHO-hSMBP2D.) As a result, it became clear that the hSMBP1 clone contained internal deletions although it covered the coding region. The present inventors succeeded in obtaining one clone that is presumed to contain the full-length sequence by analyzing a number of clones. Since the hSMBP2 clone did not contain an N terminus, the present inventors screened the human fetal heart λgt10 library as follows using the clone without the N terminus as the probe.

The present inventors screened 150,000 plaques of the Human fetal heart 5'-stretch plus cDNA library (Clontech) using the ExpressHyb Hybridization Solution (Clontech) according to the manufacturer's recommended method. An approximately 0.5 kb hSMBP2 gene fragment obtained by treating plasmid pCHO-hSMBP2D with EcoRI and BamHI was used as the probe. As a result, the present inventors obtained nine positive clones amplified one of them with the primers (GT10S1 and GT10A1; refer to Table 2) synthesized based on the internal λgt10 sequences, treated it with EcoRI, and subcloned its insert into the EcoRI site of the pCI-neo vector (Promega). The nucleotide sequence of the clone thus obtained was determined using the ABI PRISM Dye Terminator Cycle Sequencing Ready Reaction Kit with Amplitaq DNA Polymerase FS and the 377 A DNA Sequencer (Perkin-Elmer) with the synthesized sequencing primers listed below (Table 2).

TABLE 2

| Primer | Sequence |
| --- | --- |
| GT10S1 (SEQ ID NO:13) | 5'-CTTTTGAGCAAGTTCAGCCT-3' |
| GT10A1 (SEQ ID NO:14) | 5'-AGAGGTGGCTTATGAGTATTTCTT-3' |
| hSMBP2-2 (SEQ ID NO:15) | 5'-GGAAATGCTGCTGAACGTG-3' |
| hSMBP2-3) (SEQ ID NO:16) | 5'-GGGATGCCTCCAGAGGACT-3' |
| hSMBP2-4 (SEQ ID NO:17) | 5'-CCACGTTCAGCAGCATTTC-3' |
| hSMBP2-5 (SEQ ID NO:18) | 5'-GGCATCCCTACCAGCAAAT-3' |

As a result, the present inventors obtained three nearly full-length clones. Based on the analyses of the nucleotide sequence of the clones thus obtained, hSMBP1 has 195 amino acids, and its estimated molecular weight is 21643.90, while hSMBP2 has 223 amino acids, and its estimated molecular weight is 23817.09. As was expected, both proteins were found to belong to the family of membrane-bound steroid hormone binding proteins. When their deduced amino acid sequences are placed side by side, hSMBP1 shows a high degree of homology to pig PMBP, and therefore it is considered to be a human homologue (FIG. 1). A gene identical to hSMBP1 had been registered by Heidelberg University (Acc. Y12711). However, in comparison with this, the present inventors discovered two nucleotides' difference within the coding region of hSMBP1, which is considered to be caused by PCR errors. However, hSMBP2 is very similar to hSMBP1 near a C terminal, but around the N terminal, it is longer than the other proteins of the same family and has a low degree of homology. Therefore, it is presumed to be a membrane-bound protein that binds to other steroids. According to the hydrophobicity plot analysis (FIG. 2), both proteins have hydrophobic regions near their N terminus, which are then expected to contribute to the localization of the microsome fraction.

EXAMPLE 2

Analysis of the Expression of hSMBP1 and hSMBP2 in Various Tissues

The approximately 600 bp fragment obtained by treating pCOS-hSMBP1 with EcoRI-BamHI was used as the hSMBP1 probe, and the approximately 600 bp fragment obtained by treating pCHO-hSMBP2D with EcoRI-BamHI was used as the hSMBP2 probe. These probes were labeled with [α-$^{32}$P]dCTP by the random primer method using the Ready-to-Go DNA labeling beads (Pharmacia) and hybridized with the Multiple Choice Northern Blot (Human) #1 and #6 filters (OriGene Technologies) in the ExpressHyb Hybridization Solution (Clontech) according to the method recommended by the manufacturer. As a result, hSMBP1 was detected in all the tissues examined, but its expression was especially strong in the lung, the small intestine, the prostate, the testis, the ovary, the brain, the kidney, and the liver while it was weak in the muscle, the heart, the spleen, and the lymphocyte (FIG. 3A). In contrast, hSMBP2 was also detected in all the tissues examined, but its expression was especially strong in the ovary, the kidney, the liver, and the lymphocyte but weak in the brain, the heart, and the spleen (FIG. 3B).

EXAMPLE 3

In vitro Translation of hSMBP2

The present inventors obtained plasmid pCI-hSMBP2MIC by performing PCR on the hSMBP2 cDNA thus obtained using synthetic primers hSMBP2-ATG (SEQ ID NO:19: AAGAATTCCACCATGGCGGCTGGTGAT GGGGACGT) and hSMBP2MIC (SEQ ID NO:20: CCGAATTCAATGATGATGATGATGATGCAGATCCTC TTCTGAGATGAGTTTTTGTTCATCCTGTTTATTGTG ATCCTT), treating the product with restriction enzyme EcoRI, and inserting it into the EcoRI site of plasmid pCI-neo (Promega). This vector contains the T7 promoter in its N terminal upstream region and has the MIC epitope, which is recognized by an anti-Myc antibody, and the HisTag, which has six His residues, added onto the C terminus of the protein to be expressed. After the in vitro translation of the said vector according to the protocol of Single Tube Protein System 2 (Novagen), the protein was immunoprecipitated using rabbit anti-c-myc antibody (Santa cruz) and the Protein A Fast Flow (Pharmacia) and eluted with the SDS sample buffer. The supernatant of the immunoprecipitation and the sample thus obtained were subjected to SDS-PAGE and transferred onto the PVDF membrane (Bio-Rad). The color was then developed using a mouse anti-c-Myc monoclonal antibody and an anti-mouse IgG antibody coupled with alkaline phosphatase. As a result, no signal was detected from the supernatant of the immunoprecipitation or from the immunoprecipitates derived from the vector in which the hSMBP2 gene was inserted in the reverse orientation. Furthermore, a band with an apparent molecular weight of about 32,000 was detected only in the lanes that had the immunoprecipitates derived from the vector in which the hSMBP2 gene was inserted in the right orientation. The results described above confirmed the in vitro expression of the hSMBP2 gene. A possible reason for the molecular weight being about 6,000 larger than that calculated is the effect of adding the HisTag.

INDUSTRIAL APPLICABILITY

The steroid hormone binding protein of the present invention is thought to be of the membrane-bound type that differs from the usual receptors of the intranuclear transcription regulation type. This suggests that it may be involved in regulating the hormone action in the organism by a different mechanism than the intranuclear transcription regulation type receptors. Therefore, using the steroid hormone binding protein of the present invention as the target, it may be possible to develop drugs that have few side effects, by taking advantage of the difference in binding affinities between the protein of the invention and the intranuclear transcription regulation type receptors toward steroid hormones. This will make it possible to develop novel therapeutic medicines for immune-related disorders such as allergies and autoimmune diseases, and also to apply them for developing therapeutic agents against steroid-dependent malignant tumors.

What is claimed is:

1. An isolated nucleic acid encoding a polypeptide comprising an amino acid sequence at least 90% identical to SEQ ID NO:4, wherein the polypeptide specifically binds to a steroid.

2. A vector comprising the nucleic acid of claim 1.

3. A cultured host cell comprising the nucleic acid of claim 1.

4. A method of producing a polypeptide, the method comprising culturing the cultured host cell of claim 3 to produce a culture mixture, and isolating the polypeptide from the culture mixture.

5. The nucleic acid of claim 1, wherein the polypeptide has an amino acid sequence which is at least 95% identical to the amino acid sequence of SEQ ID NO:4.

6. An isolated nucleic acid encoding a polypeptide comprising the amino acid sequence of SEQ ID NO:4.

7. A vector comprising the nucleic acid of claim 6.

8. A cultured host cell comprising the nucleic acid of claim 6.

9. The isolated nucleic acid of claim 6, wherein the polypeptide consists of the amino acid sequence of SEQ ID NO:4.

10. A vector comprising the nucleic acid of claim 9.

11. A cultured host ell comprising the nucleic acid of claim 9.

12. The isolated nucleic acid of claim 6, comprising the coding sequence of SEQ ID NO:3.

13. A vector comprising the nucleic acid of claim 12.

14. A cultured host cell comprising the nucleic acid of claim 12.

15. An isolated nucleic acid encoding a polypeptide that specifically binds to a steroid and comprises the amino acid sequence of SEQ ID NO:4, with up to 20 conservative amino acid substitutions.

16. A vector comprising the nucleic acid of claim 15.

17. A cultured host cell comprising the nucleic acid of claim 15.

* * * * *

SEQUENCE LISTING

```
<160> NUMBER OF SEQ ID NOS: 22

<210> SEQ ID NO 1
<211> LENGTH: 588
<212> TYPE: DNA
<213> ORGANISM: Homo sapiens
<220> FEATURE:
<221> NAME/KEY: CDS
<222> LOCATION: (1)...(585)

<400> SEQUENCE: 1 atg gct gcc gag gat gtg gtg gcg act ggc gcc gac cca agc gat ctg      48
Met Ala Ala Glu Asp Val Val Ala Thr Gly Ala Asp Pro Ser Asp Leu
 1               5                  10                  15 gag agc ggc ggg ctg ctg cat gag att ttc acg tcg ccg ctc aac ctg      96
Glu Ser Gly Gly Leu Leu His Glu Ile Phe Thr Ser Pro Leu Asn Leu
             20                  25                  30 ctg ctg ctt ggc ctc tgc atc tcc ctg ctc tac aag atc gtg cgc ggg     144
Leu Leu Leu Gly Leu Cys Ile Ser Leu Leu Tyr Lys Ile Val Arg Gly
         35                  40                  45 gac cag ccg gcg gcc agc ggc gac agc gac gat gac gag ccg ccc cct     192
Asp Gln Pro Ala Ala Ser Gly Asp Ser Asp Asp Asp Glu Pro Pro Pro
     50                  55                  60 ctg ccc cgc ctc aag cgg cgc gac ttc acc ccc gcc gag ctg cgg cgc     240
Leu Pro Arg Leu Lys Arg Arg Asp Phe Thr Pro Ala Glu Leu Arg Arg
 65                  70                  75                  80 ttc gac ggc gtc cag gac ccg cgc ata ctc atg gcc atc aac ggc aag     288
Phe Asp Gly Val Gln Asp Pro Arg Ile Leu Met Ala Ile Asn Gly Lys
                 85                  90                  95
```

```
gtg ttc gat gtg acc aaa ggc cgc aaa ttc tac ggg ccc gag ggg ccg      336
Val Phe Asp Val Thr Lys Gly Arg Lys Phe Tyr Gly Pro Glu Gly Pro
            100                 105                 110 tat ggg gtc ttt gct gga aga gat gca tcc agg ggc ctt gcc aca ttc      384
Tyr Gly Val Phe Ala Gly Arg Asp Ala Ser Arg Gly Leu Ala Thr Phe
            115                 120                 125 tgc ctg gat aag gaa gca ctg aag gat gag tac gat gac ctt tct gac      432
Cys Leu Asp Lys Glu Ala Leu Lys Asp Glu Tyr Asp Asp Leu Ser Asp
130                 135                 140 ctc act gct gcc cag cag gag act ctg agt gac tgg gag tct cag ttc      480
Leu Thr Ala Ala Gln Gln Glu Thr Leu Ser Asp Trp Glu Ser Gln Phe
145                 150                 155                 160 act ttc aag tat cat cac gtg ggc aaa ctg ctg aag gag ggg gag gag      528
Thr Phe Lys Tyr His His Val Gly Lys Leu Leu Lys Glu Gly Glu Glu
                165                 170                 175 ccc act gtg tac tca gat gag gaa gaa cca aaa gat gag agt gcc cgg      576
Pro Thr Val Tyr Ser Asp Glu Glu Glu Pro Lys Asp Glu Ser Ala Arg
            180                 185                 190 aaa aat gat taa                                                      588
Lys Asn Asp
        195
```

<210> SEQ ID NO 2
<211> LENGTH: 195
<212> TYPE: PRT
<213> ORGANISM: Homo sapiens

<400> SEQUENCE: 2

```
Met Ala Ala Glu Asp Val Val Ala Thr Gly Ala Asp Pro Ser Asp Leu
1               5                   10                  15

Glu Ser Gly Gly Leu Leu His Glu Ile Phe Thr Ser Pro Leu Asn Leu
                20                  25                  30

Leu Leu Leu Gly Leu Cys Ile Ser Leu Leu Tyr Lys Ile Val Arg Gly
                35                  40                  45

Asp Gln Pro Ala Ala Ser Gly Asp Ser Asp Asp Glu Pro Pro Pro
        50                  55                  60

Leu Pro Arg Leu Lys Arg Arg Asp Phe Thr Pro Ala Glu Leu Arg Arg
65                  70                  75                  80

Phe Asp Gly Val Gln Asp Pro Arg Ile Leu Met Ala Ile Asn Gly Lys
                85                  90                  95

Val Phe Asp Val Thr Lys Gly Arg Lys Phe Tyr Gly Pro Glu Gly Pro
            100                 105                 110

Tyr Gly Val Phe Ala Gly Arg Asp Ala Ser Arg Gly Leu Ala Thr Phe
            115                 120                 125

Cys Leu Asp Lys Glu Ala Leu Lys Asp Glu Tyr Asp Asp Leu Ser Asp
130                 135                 140

Leu Thr Ala Ala Gln Gln Glu Thr Leu Ser Asp Trp Glu Ser Gln Phe
145                 150                 155                 160

Thr Phe Lys Tyr His His Val Gly Lys Leu Leu Lys Glu Gly Glu Glu
                165                 170                 175

Pro Thr Val Tyr Ser Asp Glu Glu Glu Pro Lys Asp Glu Ser Ala Arg
            180                 185                 190

Lys Asn Asp
        195
```

<210> SEQ ID NO 3
<211> LENGTH: 672
<212> TYPE: DNA

```
<213> ORGANISM: Homo sapiens
<220> FEATURE:
<221> NAME/KEY: CDS
<222> LOCATION: (1)...(669)

<400> SEQUENCE: 3 atg gcg gct ggt gat ggg gac gtg aag cta ggc acc ctg ggg agt ggc      48
Met Ala Ala Gly Asp Gly Asp Val Lys Leu Gly Thr Leu Gly Ser Gly
1               5                   10                  15 agc gag agc agc aac gac ggc ggc agc gag agt cca ggc gac gcg gga      96
Ser Glu Ser Ser Asn Asp Gly Gly Ser Glu Ser Pro Gly Asp Ala Gly
                20                  25                  30 gcg gca gcg gaa ggg gga ggc tgg gcg gcg gcg gcg ttg gcg ctt ctg     144
Ala Ala Ala Glu Gly Gly Gly Trp Ala Ala Ala Ala Leu Ala Leu Leu
            35                  40                  45 acg ggg ggc ggg gaa atg ctg ctg aac gtg gcg ctg gtg gct ctg gtg     192
Thr Gly Gly Gly Glu Met Leu Leu Asn Val Ala Leu Val Ala Leu Val
        50                  55                  60 ctg ctg ggg gcc tac cgg ctg tgg gtg cgc tgg ggg cgg cgg ggt ctg     240
Leu Leu Gly Ala Tyr Arg Leu Trp Val Arg Trp Gly Arg Arg Gly Leu
    65                  70                  75                  80 ggg gcc ggg gcc ggg gcg ggc gag gag agc ccc gcc acc tct ctg cct     288
Gly Ala Gly Ala Gly Ala Gly Glu Glu Ser Pro Ala Thr Ser Leu Pro
                85                  90                  95 cgc atg aag aag cgg gac ttc agc ttg gag cag ctg cgc cag tac gac     336
Arg Met Lys Lys Arg Asp Phe Ser Leu Glu Gln Leu Arg Gln Tyr Asp
            100                 105                 110 ggc tcc cgc aac ccg cgc atc ctg ctc gcg gtc aat ggg aaa gtc ttc     384
Gly Ser Arg Asn Pro Arg Ile Leu Leu Ala Val Asn Gly Lys Val Phe
        115                 120                 125 gac gtg acc aaa ggc agc aag ttc tac ggc ccg gcg ggt cca tat gga     432
Asp Val Thr Lys Gly Ser Lys Phe Tyr Gly Pro Ala Gly Pro Tyr Gly
    130                 135                 140 ata ttt gct ggt agg gat gcc tcc aga gga ctg gcc aca ttt tgc cta     480
Ile Phe Ala Gly Arg Asp Ala Ser Arg Gly Leu Ala Thr Phe Cys Leu
145                 150                 155                 160 gat aaa gat gca ctt aga gat gaa tat gat gat ctc tca gat ttg aat     528
Asp Lys Asp Ala Leu Arg Asp Glu Tyr Asp Asp Leu Ser Asp Leu Asn
                165                 170                 175 gca gta caa atg gag agt gtt cga gaa tgg gaa atg cag ttt aaa gaa     576
Ala Val Gln Met Glu Ser Val Arg Glu Trp Glu Met Gln Phe Lys Glu
            180                 185                 190 aaa tat gat tat gta ggc aga ctc cta aaa cca gga gaa gaa cca tca     624
Lys Tyr Asp Tyr Val Gly Arg Leu Leu Lys Pro Gly Glu Glu Pro Ser
        195                 200                 205 gaa tat aca gat gaa gaa gat acc aag gat cac aat aaa cag gat tga     672
Glu Tyr Thr Asp Glu Glu Asp Thr Lys Asp His Asn Lys Gln Asp
    210                 215                 220

<210> SEQ ID NO 4
<211> LENGTH: 223
<212> TYPE: PRT
<213> ORGANISM: Homo sapiens

<400> SEQUENCE: 4

Met Ala Ala Gly Asp Gly Asp Val Lys Leu Gly Thr Leu Gly Ser Gly
1               5                   10                  15

Ser Glu Ser Ser Asn Asp Gly Gly Ser Glu Ser Pro Gly Asp Ala Gly
                20                  25                  30

Ala Ala Ala Glu Gly Gly Gly Trp Ala Ala Ala Ala Leu Ala Leu Leu
            35                  40                  45
```

Thr Gly Gly Gly Glu Met Leu Leu Asn Val Ala Leu Val Ala Leu Val
    50                  55                  60

Leu Leu Gly Ala Tyr Arg Leu Trp Val Arg Trp Gly Arg Arg Gly Leu
 65                  70                  75                  80

Gly Ala Gly Ala Gly Ala Gly Glu Glu Ser Pro Ala Thr Ser Leu Pro
                85                  90                  95

Arg Met Lys Lys Arg Asp Phe Ser Leu Glu Gln Leu Arg Gln Tyr Asp
                100                 105                 110

Gly Ser Arg Asn Pro Arg Ile Leu Leu Ala Val Asn Gly Lys Val Phe
            115                 120                 125

Asp Val Thr Lys Gly Ser Lys Phe Tyr Gly Pro Ala Gly Pro Tyr Gly
    130                 135                 140

Ile Phe Ala Gly Arg Asp Ala Ser Arg Gly Leu Ala Thr Phe Cys Leu
145                 150                 155                 160

Asp Lys Asp Ala Leu Arg Asp Glu Tyr Asp Asp Leu Ser Asp Leu Asn
                165                 170                 175

Ala Val Gln Met Glu Ser Val Arg Glu Trp Glu Met Gln Phe Lys Glu
                180                 185                 190

Lys Tyr Asp Tyr Val Gly Arg Leu Leu Lys Pro Gly Glu Glu Pro Ser
            195                 200                 205

Glu Tyr Thr Asp Glu Asp Thr Lys Asp His Asn Lys Gln Asp
    210                 215                 220

<210> SEQ ID NO 5
<211> LENGTH: 34
<212> TYPE: DNA
<213> ORGANISM: Artificial Sequence
<220> FEATURE:
<223> OTHER INFORMATION: Artificially synthesized primer sequence

<400> SEQUENCE: 5
aagaattcct gcctagcgcg gcccaacctt tact                         34

<210> SEQ ID NO 6
<211> LENGTH: 34
<212> TYPE: DNA
<213> ORGANISM: Artificial Sequence
<220> FEATURE:
<223> OTHER INFORMATION: Artificially synthesized primer sequence

<400> SEQUENCE: 6
ggggatccaa aaatagatat acttccactg aatg                         34

<210> SEQ ID NO 7
<211> LENGTH: 34
<212> TYPE: DNA
<213> ORGANISM: Artificial Sequence
<220> FEATURE:
<223> OTHER INFORMATION: Artificially synthesized primer sequence

<400> SEQUENCE: 7
acggatcctg aaggcccctg actttggttg ttta                         34

<210> SEQ ID NO 8
<211> LENGTH: 21
<212> TYPE: DNA
<213> ORGANISM: Artificial Sequence
<220> FEATURE:
<223> OTHER INFORMATION: Artificially synthesized primer sequence

<400> SEQUENCE: 8
gacccaagcg atctggagag c                                         21

<210> SEQ ID NO 9
<211> LENGTH: 21
<212> TYPE: DNA
<213> ORGANISM: Artificial Sequence
<220> FEATURE:
<223> OTHER INFORMATION: Artificially synthesized primer sequence

<400> SEQUENCE: 9
ggtgaagtcg cgccgcttga g                                         21

<210> SEQ ID NO 10
<211> LENGTH: 21
<212> TYPE: DNA
<213> ORGANISM: Artificial Sequence
<220> FEATURE:
<223> OTHER INFORMATION: Artificially synthesized primer sequence

<400> SEQUENCE: 10
ctcaagcggc gcgacttcac c                                         21

<210> SEQ ID NO 11
<211> LENGTH: 18
<212> TYPE: DNA
<213> ORGANISM: Artificial Sequence
<220> FEATURE:
<223> OTHER INFORMATION: Artificially synthesized primer sequence

<400> SEQUENCE: 11
ggaagcactg aaggatga                                             18

<210> SEQ ID NO 12
<211> LENGTH: 18
<212> TYPE: DNA
<213> ORGANISM: Artificial Sequence
<220> FEATURE:
<223> OTHER INFORMATION: Artificially synthesized primer sequence

<400> SEQUENCE: 12
catccttcag tgcttcct                                             18

<210> SEQ ID NO 13
<211> LENGTH: 20
<212> TYPE: DNA
<213> ORGANISM: Artificial Sequence
<220> FEATURE:
<223> OTHER INFORMATION: Artificially synthesized primer sequence

<400> SEQUENCE: 13
cttttgagca agttcagcct                                           20

<210> SEQ ID NO 14
<211> LENGTH: 24
<212> TYPE: DNA
<213> ORGANISM: Artificial Sequence
<220> FEATURE:
<223> OTHER INFORMATION: Artificially synthesized primer sequence

<400> SEQUENCE: 14
agaggtggct tatgagtatt tctt                                      24

<210> SEQ ID NO 15
<211> LENGTH: 19
<212> TYPE: DNA

```
<213> ORGANISM: Artificial Sequence
<220> FEATURE:
<223> OTHER INFORMATION: Artificially synthesized primer sequence

<400> SEQUENCE: 15
ggaaatgctg ctgaacgtg                                                       19

<210> SEQ ID NO 16
<211> LENGTH: 19
<212> TYPE: DNA
<213> ORGANISM: Artificial Sequence
<220> FEATURE:
<223> OTHER INFORMATION: Artificially synthesized primer sequence

<400> SEQUENCE: 16
gggatgcctc cagaggact                                                       19

<210> SEQ ID NO 17
<211> LENGTH: 19
<212> TYPE: DNA
<213> ORGANISM: Artificial Sequence
<220> FEATURE:
<223> OTHER INFORMATION: Artificially synthesized primer sequence

<400> SEQUENCE: 17
ccacgttcag cagcatttc                                                       19

<210> SEQ ID NO 18
<211> LENGTH: 19
<212> TYPE: DNA
<213> ORGANISM: Artificial Sequence
<220> FEATURE:
<223> OTHER INFORMATION: Artificially synthesized primer sequence

<400> SEQUENCE: 18
ggcatcccta ccagcaaat                                                       19

<210> SEQ ID NO 19
<211> LENGTH: 35
<212> TYPE: DNA
<213> ORGANISM: Artificial Sequence
<220> FEATURE:
<223> OTHER INFORMATION: Artificially synthesized primer sequence

<400> SEQUENCE: 19
aagaattcca ccatggcggc tggtgatggg gacgt                                     35

<210> SEQ ID NO 20
<211> LENGTH: 78
<212> TYPE: DNA
<213> ORGANISM: Artificial Sequence
<220> FEATURE:
<223> OTHER INFORMATION: Artificially synthesized primer sequence

<400> SEQUENCE: 20
ccgaattcaa tgatgatgat gatgatgcag atcctcttct gagatgagtt tttgttcatc         60
ctgtttattg tgatcctt                                                        78

<210> SEQ ID NO 21
<211> LENGTH: 194
<212> TYPE: PRT
<213> ORGANISM: Suidae

<400> SEQUENCE: 21

Met Ala Ala Glu Asp Val Ala Ala Thr Gly Ala Asp Pro Ser Glu Leu
```

```
              1               5                  10                 15
            Glu Gly Gly Gly Leu Leu His Glu Ile Phe Thr Ser Pro Leu Asn Leu
                         20                  25                 30

Leu Leu Leu Gly Leu Cys Ile Phe Leu Leu Tyr Lys Ile Val Arg Gly
                     35                  40                  45

Asp Gln Pro Ala Ala Ser Asp Ser Asp Asp Glu Pro Pro Leu
                 50                  55                  60

Pro Arg Leu Lys Arg Arg Asp Phe Thr Pro Ala Glu Leu Arg Arg Phe
             65                  70                  75                  80

Asp Gly Val Gln Asp Pro Arg Ile Leu Met Ala Ile Asn Gly Lys Val
                             85                  90                  95

Phe Asp Val Thr Lys Gly Arg Lys Phe Tyr Gly Pro Glu Gly Pro Tyr
                         100                 105                110

Gly Val Phe Ala Gly Arg Asp Ala Ser Arg Gly Leu Ala Thr Phe Cys
                         115                 120                 125

Leu Asp Lys Glu Ala Leu Lys Asp Glu Tyr Asp Asp Leu Ser Asp Leu
                 130                 135                 140

Thr Pro Ala Gln Gln Glu Thr Leu Asn Asp Trp Asp Ser Gln Phe Thr
            145                 150                 155                 160

Phe Lys Tyr His His Val Gly Lys Leu Leu Lys Glu Gly Glu Pro
                         165                 170                 175

Thr Val Tyr Ser Asp Glu Glu Pro Lys Asp Glu Ser Ala Arg Lys
                         180                 185                 190

Asn Asp

<210> SEQ ID NO 22
<211> LENGTH: 223
<212> TYPE: PRT
<213> ORGANISM: Rattus rattus

<400> SEQUENCE: 22

Met Ala Ala Glu Asp Val Val Ala Thr Gly Ala Asp Pro Ser Glu Leu
             1               5                  10                 15

Glu Gly Gly Gly Leu Leu Gln Glu Ile Phe Thr Ser Pro Leu Asn Leu
                         20                  25                 30

Leu Leu Leu Gly Leu Cys Ile Phe Leu Leu Tyr Lys Ile Val Arg Gly
                     35                  40                  45

Asp Gln Pro Gly Ala Ser Gly Asp Asn Asp Asp Glu Pro Pro Pro
                 50                  55                  60

Leu Pro Arg Leu Lys Pro Arg Asp Phe Thr Pro Ala Glu Leu Arg Arg
             65                  70                  75                  80

Tyr Asp Gly Val Gln Asp Pro Arg Ile Leu Met Ala Ile Asn Gly Lys
                             85                  90                  95

Val Phe Asp Val Thr Lys Gly Arg Lys Phe Tyr Gly Pro Glu Gly Pro
                         100                 105                110

Tyr Gly Val Phe Ala Gly Arg Asp Ala Ser Arg Gly Leu Ala Thr Phe
                         115                 120                 125

Cys Leu Asp Lys Glu Ala Leu Lys Asp Glu Tyr Asp Asp Leu Ser Asp
                 130                 135                 140

Leu Thr Pro Ala Gln Gln Glu Thr Leu Asn Asp Trp Asp Ser Gln Phe
            145                 150                 155                 160

Ser Ser Pro Ser Ser Thr Ile Thr Trp Gly Lys Leu Leu Glu Gly Ala
                         165                 170                 175
```

-continued

```
Glu Glu Pro Ile Val Tyr Ser Asp Asp Glu Glu Gln Lys Met Arg Leu
            180                 185                 190

Leu Gly Arg Val Thr Glu Ala Val Ser Gly Ala Tyr Leu Phe Leu Tyr
        195                 200                 205

Phe Ala Lys Ser Phe Val Thr Phe Gln Ser Val Phe Thr Thr Trp
        210                 215                 220
```